United States Patent [19]
Young et al.

[11] Patent Number: 5,817,017
[45] Date of Patent: Oct. 6, 1998

[54] MEDICAL DEVICES AND MATERIALS HAVING ENHANCED MAGNETIC IMAGES VISIBILITY

[75] Inventors: Stuart W. Young; Richard A. Miller, both of Portola Valley, Calif.

[73] Assignee: Pharmacyclics, Inc., Sunnyvale, Calif.

[21] Appl. No.: 446,652

[22] PCT Filed: Apr. 12, 1994

[86] PCT No.: PCT/US94/04011

§ 371 Date: May 24, 1995

§ 102(e) Date: May 24, 1995

[87] PCT Pub. No.: WO94/23782

PCT Pub. Date: Oct. 27, 1994

[51] Int. Cl.⁶ .................................. A61B 05/055
[52] U.S. Cl. ........................ 600/433; 600/420; 424/9.3
[58] Field of Search ................. 128/654, 653.4, 128/658, 656; 424/9.3, 9.4; 600/420, 433

[56] References Cited

U.S. PATENT DOCUMENTS

| | | |
|---|---|---|
| 4,027,659 | 6/1977 | Slingluff . |
| 4,781,198 | 11/1988 | Kanabrocki . |
| 4,827,931 | 5/1989 | Longmore . |
| 4,967,764 | 11/1990 | Basser . |
| 4,989,608 | 2/1991 | Ratner . |
| 5,016,639 | 5/1991 | Allen . |
| 5,023,072 | 6/1991 | Cheng . |
| 5,122,363 | 6/1992 | Balkus, Jr. et al. . |
| 5,154,179 | 10/1992 | Ratner . |
| 5,171,232 | 12/1992 | Castillo et al. . |
| 5,201,314 | 4/1993 | Bosley et al. . |
| 5,234,416 | 8/1993 | Macaulay et al. . |
| 5,330,742 | 7/1994 | Deutsch et al. . |
| 5,394,457 | 2/1995 | Leibinger et al. . |
| 5,437,290 | 8/1995 | Bolger et al. ............................ 128/989 |

OTHER PUBLICATIONS

Chambron, C. et al. "Superparamagnetic Iron Oxides As Positive MR Contrast Agents; In Vitro and In Vivo Evidence," *Magnetic Resonance Imaging*, (1930) 11:509–519.

Engelstad, B. L. et al. "Contrast Agents," *MRI*, (1988) Chapter 9, pp. 161–181.

Fahlvik, A. et al. "Iron Oxides as MR Imaging Contrast Agents[1]," (1993) JMRI 3:187–194.

Rubin, D. et al. "Magnetic Susceptibility Effects and Their Application in the Development of New Ferromagnetic Catheters for Magnetic Resonance Imaging,"(1990) *Investigative Radiology* 25 (12) :1325–1332.

*Primary Examiner*—Marvin M. Lateef
*Assistant Examiner*—Shawna J. Shaw
*Attorney, Agent, or Firm*—Townsend and Townsend and Crew LLP

[57] ABSTRACT

Catheters and other medical devices include a non-metallic member having paramagnetic ionic particles fixedly incorporated therethrough in order to provide enhanced detectability when viewed by magnetic imaging regardless of the orientation of the non-metallic member in the magnetic field. Catheters are usually formed from polymeric tubing, and the paramagnetic ionic particles are usually formed from paramagnetic ions incorporated with water or other proton-donating fluid into carrier particles, such as zeolites, molecular sieves, clays, synthetic ion exchange resins, and microcapsules. Catheters and other medical devices include a non-metallic member having small iron and/or superparamagnetic particles fixedly incorporated therethrough or thereover in order to provide enhanced detectability when viewed by magnetic imaging. Catheters are usually formed from polymeric tubing, and the iron and/or superparamagnetic particles at or near the surface of the catheter interact with the water protons of the surrounding patient's body to provide image enhancement regardless of the orientation of the polymeric or other non-metallic material in the magnetic field.

69 Claims, 2 Drawing Sheets

MEDICAL DEVICES AND MATERIALS HAVING ENHANCED MAGNETIC IMAGES VISIBILITY

BACKGROUND OF THE INVENTION

1. Field of the Invention

The present invention relates generally to magnetic imaging of insertable and implantable devices within or on a patient's body. More particularly, the present invention relates to the fabrication and use of such devices having properties which enhance their image when viewed by magnetic resonance imaging and other imaging techniques.

The ability to non-invasively image internal body structures and diseased tissues within a patient's body has become indispensable to the practice of modern medicine. A variety of such non-invasive imaging techniques exist, including x-ray imaging, ultrasonic imaging, x-ray computed tomography, emission tomography, and the like. Of particular interest to the present invention, magnetic resonance imaging can provide two-dimensional sectional images through a patient, providing color or gray scale contrast images of soft tissue, particularly for imaging tumors, edema, infarcts, infections, and the like. In addition to high quality, magnetic resonance images are desirable since they do not expose the patient to harmful radiation.

Patients undergoing magnetic resonance imaging often have catheters, tubes, implants, and other devices present within their bodies, and the precise anatomical locations of such devices can be of substantial clinical importance. Unfortunately, most catheters and many other devices are composed of materials, such as organic polymers, which do not produce adequate signals for detection by magnetic resonance imaging techniques. In particular, most polymeric catheters are not clearly discernible on magnetic resonance images unless they are surrounded by tissue that has a high signal intensity, in which case they leave a dark void on the image.

It would therefore be desirable to provide catheters and other medical devices having enhanced detectability when viewed using magnetic resonance imaging regardless of the nature of surrounding tissue. To this end, it has been proposed to incorporate ferromagnetic particles within the polymeric tubes which are employed in a variety of catheter devices. The ferromagnetic particles could be incorporated during the extrusion of such tubes, and would provide a high contrast image when viewed under magnetic resonance imaging. While the use of ferromagnetic particles in catheters would provide for improved visibility, such improvement is dependent on the relative orientation of the catheter relative to the magnetic field used in imaging. In particular, it has been found that the image enhancement occurs only when the catheter is oriented perpendicular to the main magnetic field. When oriented parallel to the magnetic field, there is no image enhancement. Image enhancement using ferromagnetic particles does not depend on an interaction with protons. Thus, further improvements in magnetic resonance image enhancement of catheters and other medical devices would be desirable.

It has also been proposed to introduce liquid solutions and gels containing paramagnetic material into catheter lumens. The paramagnetic material will provide contrast with surrounding tissue regardless of orientation relative to the magnetic field. Although this is an improvement in one sense over the use of ferromagnetic materials as discussed above, the need to incorporate a liquid or gel in the catheter is difficult from a manufacturing view, limits the flexibility of the catheter, and is generally inconvenient.

Direct incorporation of paramagnetic materials into the polymeric material of catheters and other medical devices, however, is difficult since paramagnetic materials, such as transition metal ions, require the proximity of water or other proton-bearing substance in order to provide a high contrast signal under magnetic resonance imaging. The introduction of hydrated transition metal ions into extruded materials is particularly problematic since the water of hydration will be readily lost during high temperature extrusion.

A method has been proposed for highlighting the magnetic resonance image of certain tissues, e.g. liver tumors, by the injection of suspensions of superparamagnetic particles in a patient's body. Superparamagnetic particles provide a substantially greater contrast with surrounding tissue than would equivalent paramagnetic solutes, and interact with water-adjacent protons without the formation of aqueous solutions of superparamagnetic particles. The particles, however, must interact directly with water protons to produce the image enhancement.

For these reasons, it would be desirable to provide catheters and other medical devices having enhanced visibility when viewed under magnetic resonance and other magnetic imaging, regardless of orientation of the devices relative to the main magnetic field. Such catheters and devices should not require the entrapment of a liquid or gel, and should be relatively easy to manufacture. It would be further desirable to provide for the incorporation of paramagnetic materials, such as hydrated transition metal ions, into the polymeric components of a catheter or other medical device without the loss of hydration.

2. Description of the Background Art

Medical catheters incorporating ferromagnetic materials to enhance magnetic resonance imaging are described in Rubin et al. (1990) Inves. Radiol. 25:1325–1332, and U.S. Pat. Nos. 5,154,179 and 4,989,608. Rubin et al. disclose that the magnetic image of such catheters containing ferromagnetic materials is not enhanced when the catheters are oriented parallel to the magnetic field. The '179 and '608 patents further describe introduction of an aqueous liquid or gel incorporating a paramagnetic agent into a catheter lumen to further enhance such imaging. U.S. Pat. No. 5,122,363, describes use of zeolite-enclosed paramagnetic ions as image brightening or image contrast agents in magnetic resonance imaging. The full disclosures of each of the above patents are incorporated herein by reference. In addition, Contrast Agents, Barry L. Engelstad and Gerald L. Wolf, in MRI, C. V. Mosby, St. Louis, Chapter 9, pages 161–181 (1988), describes the use of superparamagnetic particles for the highlighting of liver tumors. The use of superparamagnetic and other iron oxide particles as MRI contrast agents is described in Fahlvik et al. (1993) JMRI 3:187–194, and Chambron et al. (1993) Magn. Reson. Imaging 11:509–519.

SUMMARY OF THE INVENTION i. Paramagnetic ionic particles

According to the present invention, articles such as catheters and other medical devices comprise non-metallic members having paramagnetic ionic particles fixedly incorporated therein. The term "paramagnetic ionic particles" as used herein and in the appended claims refers to particles which comprise a paramagnetic cation incorporated or encapsulated together with water or another proton-donating fluid in a carrier particle such as an ion exchange resin or a microcapsule. The non-metallic members are usually composed of an organic polymer, and would in the absence of the paramagnetic ionic particles be poorly visible when viewed by magnetic imaging methods, such as magnetic resonance imaging, magnetic resonance spectroscopic imaging and biomagnetometry. It has been found that the magnetic resonance signal intensity of such articles can be greatly enhanced by incorporating paramagnetic ionic particles into all or a portion of the non-metallic members. In particular, it has been found that suitable paramagnetic ionic particles can be combined with suitable polymeric materials and extruded into a desired shape, such as a flexible tube, without substantial loss of proton-donating fluid, which is essential for image enhancement via the paramagnetic metals.

In a particular aspect, the present invention comprises a catheter including a tubular member composed of an organic polymer. The paramagnetic ionic particles are fixedly incorporated and dispersed in selected portions of the tubular member at a concentration selected to enhance detectability when viewed with magnetic imaging techniques. Paramagnetic ionic particles may be dispersed uniformly throughout the catheter, or may be dispersed in a preselected pattern, such as one or more circumferential bands or an axial band extending partly or wholly along the length of the tubular member.

In a further aspect, the present invention comprises methods for fabricating elongate polymeric tubes having an enhanced magnetic image. The method includes combining paramagnetic ionic particles, as defined herein, with a polymeric material, such as a polyethylene, a polyurethane, a polyvinyl chloride, a nylon, a latex, a silicone rubber, halogenated polyethylenes (e.g., polytetrafluoroethylene (PTFE) and other Teflon® materials), organosilicones (e.g., Silastic® materials), or the like. The combined particles and polymeric material may then be formed into a tube by conventional techniques, such as extrusion at elevated temperatures. Surprisingly, it has been found that the proton-donating fluid in the paramagnetic ionic particle is not lost during such extrusion or other fabrication steps.

In a still further aspect, the present invention comprises compositions useful for forming articles having enhanced magnetic images. The compositions comprise a polymeric material and paramagnetic ionic particles fixedly incorporated in the polymeric material. Presently preferred paramagnetic ionic particles are paramagnetic metal ions incorporated into hydrated ion exchange resins, such as natural zeolites, molecular sieves, clays, and synthetic ion exchange resins. Such compositions are suitable for fabrication into elongate polymeric tubes, as described above, and other organic polymeric articles.

A method for imaging according to the present invention comprises introducing to a patient's body an article including a non-metallic member having paramagnetic ionic particles fixedly incorporated therein. The body is viewed using a magnetic imaging device, such as magnetic resonance imaging devices and biomagnetic imaging devices, and the article produces an image having enhanced visibility at all orientations relative to the imaging device. The article may comprise a catheter, an implant, or other conventional medical device. Usually, the non-metallic member will be composed of an organic polymer and the paramagnetic ionic particles will comprise paramagnetic metal ions entrapped in a carrier particle, such as an ion exchange resin, together with a proton-donating fluid, such as water.

The use of paramagnetic ionic particles has a number of advantages when compared to previous methods and compositions for magnetic resonance image enhancement. The image signal produced by articles incorporating such paramagnetic ionic particles is very intense, with minimum blurring and minimum presence of an image corona. In contrast, the use of ferromagnetic particles can cause a corona to appear in the image artifact, making precise location of the article within the imaged area difficult. Moreover, the image artifact produced by the present invention is orientation independent, with equally clear images being available regardless of the relative orientation of the article to the magnetic resonance imaging device. The paramagnetic ions can provide for a very high signal intensity, and the image artifact produced will be white or bright, rather than black as with the use of ferromagnetic ions. The paramagnetic ionic particles provide for the retention of paramagnetic ions and relatively large amounts of water or other proton-donating fluid, which together provide for a high level of image enhancement.

ii. Small iron particles

In another aspect of the present invention, articles such as catheters and other medical devices comprise non-metallic members having very small iron particles, of 20 $\mu$m or less, preferably superparamagnetic particles, fixedly incorporated therein. The non-metallic members are usually composed of an organic polymer and would, in the absence of the iron or superparamagnetic particles, be poorly visible when viewed by magnetic imaging methods, such as magnetic resonance imaging, magnetic resonance spectroscopic imaging and biomagnetometry. It has been found that the magnetic resonance signal intensity of such articles can be greatly enhanced by incorporating such iron and/or superparamagnetic particles into all or a portion of the non-metallic members. In particular, it has been found that suitable small iron and/or superparamagnetic particles incorporated into polymeric materials and extruded into a desired shape, such as a flexible tube, will, when inserted into a patient's body, interact with the surrounding water protons to produce image enhancement. The resultant image enhancement is irrespective of the relative orientation of the tube or other article to the magnetic field. It is frequently desirable that the concentration of the particles be limited to or concentrated at or near an outer or inner exposed surface of the article in order to reduce the distance between the particles and surrounding aqueous fluid, thereby intensifying their action on surrounding water protons and thus increasing the image enhancement. Thus, in a presently preferred embodiment, the particles are dispersed at least at or near an exposed surface of the article. By "exposed surface" it is thus meant that the surface will become exposed to an aqueous medium, usually a body fluid or tissue, during normal use of the device.

In a particular aspect, the present invention comprises a catheter including a tubular member composed of an organic polymer. The superparamagnetic or small iron particles are fixedly incorporated and dispersed in selected portions of the tubular member at a concentration selected to enhance detectability by means of magnetic resonance imaging techniques, regardless of the orientation of the tubular member in the magnetic field, when the tubular member is within a patient's body. The particles may be dispersed uniformly throughout the catheter, or may be dispersed in a preselected pattern, such as a circumferential band or an axial band extending partly or wholly along the length of the tubular member. It is often desirable that the distribution of the particles be limited to or concentrated at or near an outer or inner exposed surface of the catheter. Thus, it is desirable, in a presently preferred embodiment, that the small iron particles be dispersed at least at or near an exposed surface. The exposed surface will be a surface that becomes exposed to a body fluid or a fluid disposed within the lumen of the catheter.

In a further aspect, the present invention comprises methods for fabricating elongate polymeric tubes having an enhanced magnetic image. The method includes combining the small iron and/or superparamagnetic particles with a polymeric material, such as a polyethylene, a polyurethane, a polyvinyl chloride, a nylon, a latex, a silicone rubber, halogenated polyethylenes (e.g., polytetrafluoroethylene (PTFE) and other Teflon® materials), organosilicones (e.g., Silastic® materials), or the like. The combined particles and polymeric material may then be formed into a tube by conventional techniques such as extrusion. It may also be possible to impregnate particles directly into, or coat particles over, the exterior of an article after fabrication. Surprisingly, it has been found that the iron and/or superparamagnetic particles located at, over, or very near the surface of the tube will interact with the water protons of a surrounding patient's body to produce superparamagnetic magnetic image enhancement. It has also been found that this image enhancement is independent of the orientation of the magnetic field.

In a still further aspect, the present invention comprises compositions useful for forming articles having enhanced magnetic images. The compositions comprise a polymeric material and small iron and/or superparamagnetic particles fixedly incorporated therein. Such compositions are suitable for fabrication into elongate polymeric tubes, as described above, and other organic polymeric articles. A method for imaging according to the present invention comprises introducing to a patient's body an article including a non-metallic member having small iron and/or superparamagnetic particles fixedly incorporated therein or thereover. The body is viewed using a magnetic imaging device, such as magnetic resonance imaging devices or biomagnetic imaging devices, and the article produces an image having enhanced visibility at all orientations relative to the imaging device. The article may comprise a catheter, an implant, or other conventional medical device. Usually, the non-metallic member will be composed of an organic polymer and the small iron and/or superparamagnetic particles will be dispersed therein, preferably being concentrated near the surface, or coated thereover.

The use of small iron and/or superparamagnetic particles has a number of advantages when compared to previous methods and compositions for magnetic image enhancement. The image signal produced by articles incorporating such superparamagnetic particles is very intense. Moreover, the image produced by the present invention is orientation independent, with clear images being available regardless of the relative orientation of the article to the magnetic resonance imaging device. The superparamagnetic behavior provides for a very high signal intensity, and the image signal produced will be white or bright, rather than a white and black artifact which is produced with the use of larger ferromagnetic particles. The superparamagnetic particles at or near the surface of the article interact with the water protons of a surrounding patient's body, eliminating the need to incorporate liquid solutions or gels into the catheter itself, as has been required for image enhancement with paramagnetic ions.

A further understanding of the nature and advantages of the invention will become apparent by reference to the remaining portions of the specification and drawings.

DESCRIPTION OF THE PREFERRED EMBODIMENT

Figure 1:
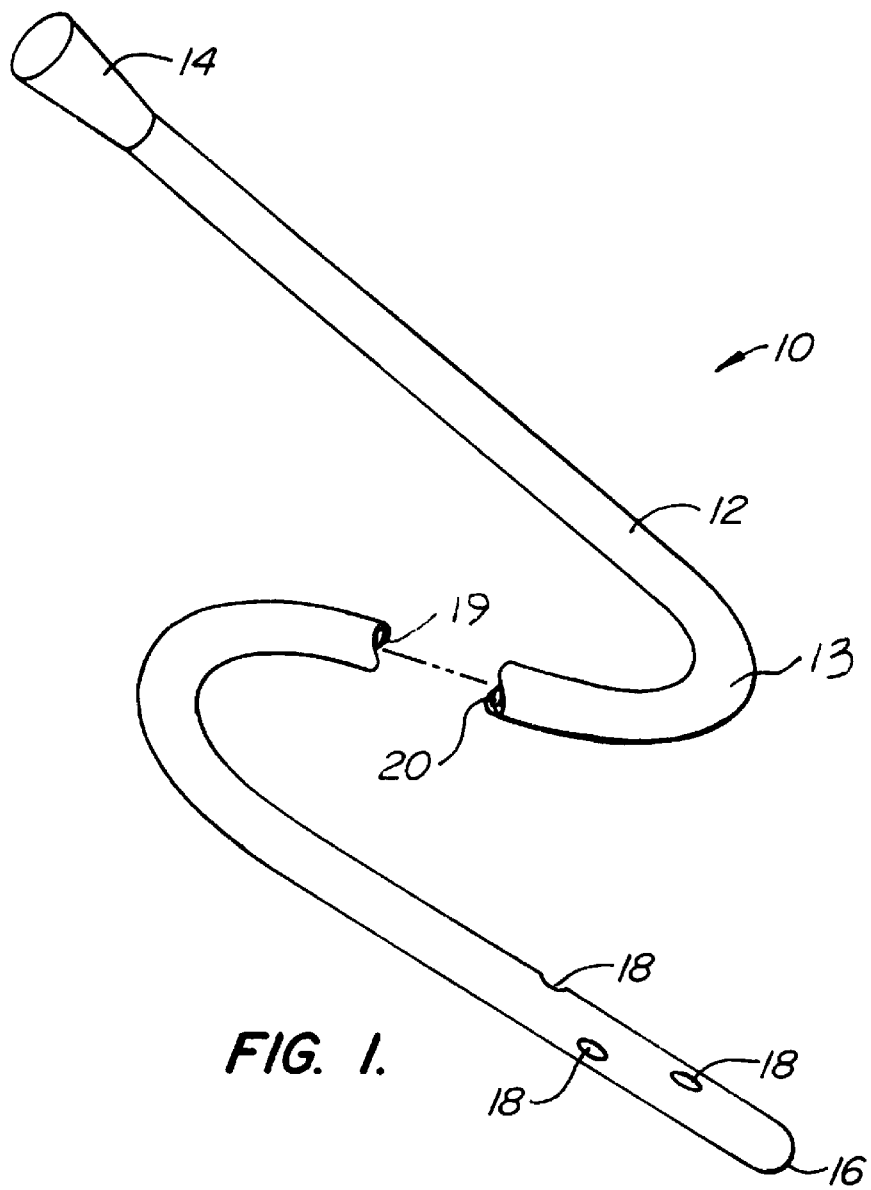
FIG. 1 illustrates a simple drainage or perfusion catheter comprising a flexible polymeric body, constructed in accordance with the principles of the present invention.

The present invention is useful for enhancing the magnetic images of a wide variety of insertable and implantable medical devices which would otherwise be difficult to discern during magnetic imaging procedures. The magnetic images will be produced by known magnetic imaging techniques, such as magnetic resonance imaging (MRI), magnetic resonance spectroscopic imaging (MRSI) and biomagnetometry (see, Moshage et al. (1991) Radiology 180:685, and Scheider et al. (1990) Radiology 176:825). The present invention is particularly useful for modifying conventional catheters, feeding tubes, drainage tubes, shunts, and other devices which comprise polymeric tubes, as well as interventional devices, such as for suturing or biopsy, which devices may be temporarily introduced to a patient body lumen or tissue. The present invention will also be suitable for modifying portions or components of permanently implantable devices, such as joint and other prostheses, breast implants, pacemakers, drug injection ports, pediatric intercardiac devices, drug delivery devices, and the like, where it is desirable that the presence and location of the device be readily discernible during subsequent magnetic imaging procedures.

The articles or devices of the present invention will include a non-metallic element which will usually comprise a primary component of the device. In the case of simple tubular devices, the non-metallic element will usually be a polymeric tube which defines the primary body of the device. In the case of more complex devices, the non-metallic element may be any component where it is desirable to enhance visibility under magnetic imaging. Such non-metallic components will usually be composed of organic polymers, but may also be ceramics, composites, or any other biocompatible material which does not produce the desired magnetic resonance imaging artifact and which can be modified to incorporate the paramagnetic ionic particles or the small iron and/or superparamagnetic particles of the present invention, as described in more detail below. Exemplary organic polymers include those from the group consisting of polyethylene, polyurethane, polyvinylchloride, nylon, latex, silicone rubber, halogenated polyethylenes (e.g., polytetrafluoroethylene (PTFE) and other Teflon® materials), organosilicones (e.g., Silastic® materials), and the like. This list, however, is not meant to be exhaustive and a wide variety of other organic polymers would be available to fabricate non-metallic elements according to the present invention.

In one aspect of the invention, the polymer is a hydrated polymeric material having a water content of from about 0.001 wt % to about 50 wt %, preferably of from about 5 wt % to about 20 wt %. These hydrated polymers provide additional water within the polymeric matrix in close proximity to the incorporated paramagnetic ions or the small iron and/or superparamagnetic particles to provide increased magnetic image enhancement.

The non-metallic elements and the articles of the present invention will usually be substantially free from ferromagnetic particles, and particularly ferromagnetic particles having a size larger than 20 μm. Such ferromagnetic particles are unnecessary to provide for magnetic image enhancement according to the present invention, and their elimination will reduce or avoid the blurring and image corona effect which have been previously observed in association with their use. See, Rubin et al. (1990), supra.

The non-metallic elements and the articles of the present invention may optionally comprise radiopaque materials to enhance their image under x-ray scanning and related techniques, such as fluoroscopy, computer tomography, and the like. Generally, radiopaque materials can be incorporated or impregnated into the device, either uniformly or in localized areas, in the form of stripes, bands, and the like. Suitable radiopaque materials include barium, bismuth, and other radiodense salts, as described in U.S. Pat. Nos. 3,529,633; 3,608,555; and 2,857,915, the disclosures of which are incorporated herein by reference. Preferred is the use of barium sulfate or other barium salts which have been found to be completely compatible with the paramagnetic ionic particles of the present invention. It will also be possible to place discrete radiopaque markers on the medical devices, such as radiopaque gold or platinum bands placed around catheter tubes.

The paramagnetic ionic particles according to the present invention will comprise a paramagnetic cation incorporated or encapsulated together with a proton-donating fluid in a carrier particle. The paramagnetic ion may be any metal ion displaying paramagnetic properties, typically being an element of atomic numbers 21–29, 42, 44, and 58–70. Exemplary transition metal cations include $Gd^{+3}$, $V^{+4}$, $V^{+3}$, $Cu^{+2}$, $Ni^{+2}$, $Cr^{+3}$, $Co^{+3}$, $Co^{+2}$, $Cr^{+3}$, $Fe^{+3}$, $Fe^{+2}$, and the like. The cations will normally be in the form of a salt, including sulfates, chlorides, acetates, nitrates, and the like, as counter ions.

Proton-donating fluids suitable for use in the present invention are those fluid materials which provide observable protons for constructing a magnetic resonance image. Suitable proton-donating fluids include, but are not limited to, water, alcohols such as glycols (e.g., propylene glycol, polyethylene glycol and ethylene glycol), glycerols, detergents such as sulfonated compounds, ethers such as glyme and diglyme, amines, imidazoles, and Tris. In one presently preferred embodiment, the proton-donating fluid has a boiling point equal to or, more preferably, greater than the boiling point of water. Presently preferred proton-donating fluids are water and polyethylene glycol.

The carrier particles comprising the paramagnetic ionic particles will enclose and protect the paramagnetic ions during fabrication of the image-enhanced article according to the methods of the present invention and will maintain the paramagnetic ions in close proximity to the proton-donating fluid. The carrier particle will usually be a charged ion exchange resin capable of binding the paramagnetic ions and fluid under the conditions of the fabrication process. Suitable carrier particles include natural and synthetic zeolites and other molecular sieves, clays, and other macroreticular ion exchange resins capable of entrapping and binding the paramagnetic ions and proton-donating fluid.

Particularly useful carrier particles for the practice of the invention include the zeolites, of which there are numerous examples that can be used for the entrapment of paramagnetic ions. Particularly useful are the synthetic zeolites type A, type X, type Y, and natural zeolite ZSM-5, as described in Breck, *Zeolite Molecular Sieves*, Krieger Publishing Company, Malabar, Fla. (1984) and in U.S. Pat. No. 4,388,285, the full disclosure of which is incorporated herein by reference. Materials similar to zeolites may be used as the carrier particle. For example, molecular sieves, which are structurally similar to zeolites, and especially those molecular sieves that possess ion exchange properties, may be used analogously to zeolites.

Particularly suitable clays for use as carrier particles include the general class of smectite clays, of which Hectorite and montmorillonite clays are examples (see, U.S. Pat. No. 5,277,896, the full disclosure of which is incorporated herein by reference).

Exemplary synthetic ionic exchange resin particles are described in U.S. Pat. Nos. 4,297,270; 4,256,840; 4,224,415; 4,382,124; and 4,501,826, the full disclosures of which are incorporated herein by reference.

In addition to zeolite- or clay-enclosed "free" paramagnetic metal ions, it has been discovered that useful imaging compositions may be obtained from zeolite- or clay-enclosed metal ion chelate complexes. The paramagnetic ion chelates may be formed in situ, that is, after the ion is enclosed within the zeolite or clay, or metal ion complexes may be enclosed by synthesizing the zeolite or clay around a metal ion chelate. Sodium type A and type X zeolites readily form around gadolinium(III) complexes of 8-hydroxyquinoline, dipiconilic acid and phthalic acid. Other suitable ligands may include salicylamide, salicylic acid, anthranilic acid, bipyridine, terpyridine, phenanthroline, ethylenediamine, bis(salicylaldehyde) ethylenediamine, ethylenediamine diacetic acid, the texaphyrins (described in U.S. Pat. Nos. 4,935,498 and 5,252,720), or the like. Chelated paramagnetic species, as a general rule, are larger than the free ion and therefore must be located in the larger spaces within the zeolite structure. Consequently, the paramagnetic ion is more accessible to water or other proton-donating fluid than ions located in smaller spaces. See, U.S. Pat. No. 5,277,896 and PCT publication WO 92/10213, the full disclosures of which are incorporated herein by reference.

The ion exchange resin carrier particle containing the paramagnetic ions and the proton-donating fluid may optionally be coated or encapsulated with a suitable material, usually a polymer, to form a shell or film in order to further enclose and protect the paramagnetic ions and the associated proton-donating fluid during manufacture of the devices or articles of the present invention. Polymers suitable for use as coatings can include, but are not limited to, cellulose ethers, such as hydroxypropyl cellulose and hydroxypropyl methylcellulose; acrylics such as methacrylate and methyl-methacrylate copolymers, and methacrylic acid ester copolymers with acidic ionizable groups; ethylcellulose alone or in combination with a cellulose ether; cellulose acetate; hydroxypropyl methylcellulose phthalate; polyvinyl acetate phthalate; cellulose acetate phthalate; shellac; zein; and the like. The method of coating is not critical, and the coating can be accomplished by methods known in the art, such as for example spray-coating, spin-coating, deposition-coating, solvent evaporation, coacervation and other encapsulation procedures, and the like.

The carrier particle may alternatively be a microcapsule, which comprises a thin coating that surrounds and encloses a small droplet of the paramagnetic ions and the proton-donating fluid. Such microcapsules and their preparation are well known in the art.

The paramagnetic ions will be incorporated into the carrier particles by conventional techniques. For example, where the carrier particle is an ion exchange resin, typically the paramagnetic ions will be mixed with the ion exchange resin carrier in an aqueous or other proton-donating fluid solution at moderate temperatures, typically from room temperature to 40° C., for extended periods, typically from 2 to 24 hours. The mixture is stirred, and the paramagnetic ions will be taken up into the porous structure of the ion exchange resin over time. Typically, the ion exchange resins can be loaded to contain from 0.1% to 20% paramagnetic ion by weight, typically from 0.5% to 15%, usually from 1% to 10% by weight. The ion exchange resins will typically include from 10% to 30% water by weight, depending on the nature of the resin. The resulting suspension can be filtered and washed to remove any free paramagnetic ion and/or cation which remains. The resulting paramagnetic ionic particles are suitable for incorporation into the articles of the present invention by the methods described below.

Where the carrier particle is a microcapsule, the microcapsule may be prepared by known procedures, such as coacervation, phase separation, interfacial polymerization or electrostatic methods. For example, paramagnetic ions and a proton-donating fluid are mixed together and the solution is then finely dispersed in a liquid with which it is substantially immiscible to form a two-phase system. Thus, where the proton-donating fluid is water, the immiscible liquid will preferably be an organic solvent to create a water-in-oil emulsion. The immiscible liquid includes a polymer or other suitable coating material capable of forming a wall. The system is agitated until the required drop size of ions/fluid is obtained. Thereafter, the system is treated to cause the wall-forming material to come out of solution and deposit around each drop of ions/fluid, whereby the formation of a capsule shell around the finely dispersed ion-containing internal phase is caused, giving a microcapsule. Depending on the wall-forming material used, the transition from soluble to insoluble can be initiated and finalized by a variety of steps known in the art, such as heating and/or cooling, pH adjustment, addition of a substituent(s) that react with the wall-forming material to form high molecular weight products, or addition of curing catalysts. The wall-forming material should be chosen to not melt or dissolve under the conditions of manufacture of the articles of the invention, as discussed herein.

A particularly preferred paramagnetic ionic particle is trivalent gadolinium incorporated in a type Y synthetic zeolite at a loading of metal ion in the range from about 2% to 10% metal ion by weight. Specific methods for preparing preferred trivalent gadolinium-type A, -type X and -type Y zeolite aggregates are described in U.S. Pat. No. 5,122,363, the full disclosure of which is incorporated herein by reference.

The paramagnetic ionic particles will be fixedly incorporated into the non-metallic member of the article of the present invention during fabrication. By "fixedly incorporated," it is meant that the paramagnetic ionic particles containing proton-donating fluid are dispersed directly within the material matrix of the non-metallic member. This may be accomplished by various conventional techniques, such as impregnation, lamination, coating, compounding, or the like. In the case of organic polymers, fixed incorporation will preferably be accomplished by combining the paramagnetic ionic particles with a suitable polymeric material prior to forming it to the desired article, typically by extrusion, injection molding, or the like. The fixed incorporation of the paramagnetic ionic particles according to the present invention is in contrast to the temporary introduction of a liquid or gel form of a paramagnetic material which can be introduced into a catheter lumen but not incorporated into the polymeric material of the catheter itself, as taught in U.S. Pat. Nos. 5,154,179 and 4,989,608, discussed above.

The paramagnetic ionic particles will be incorporated in the non-metallic member in an amount or concentration sufficient to achieve the desired image enhancement. The particular amount or concentration depends on the concentration of the paramagnetic ions in the carrier particle, the nature of the non-metallic material, and a variety of other factors, but will usually be in the range from 0.1% to 20% by weight, more usually being in the range from 1% to 10% by weight, and frequently being in the range from 1% to 5% by weight.

Exemplary flexible tubes may be prepared according to the method of the present invention using conventional extrusion equipment and techniques. Such extruders utilize polymeric materials and, by applying heat and pressure, form the materials to a continuous length of tubing having a desired diameter, a wall thickness, and the like. The paramagnetic ionic particles of the present invention may be incorporated into such tubes simply by mixing the ionic particles with the polymeric starting material prior to extrusion. Uniform dispersion of the paramagnetic ions can thus be achieved by completely mixing and dispersing the ion-containing carrier particles within the polymeric material at the desired weight and concentration and extruding the mixture in an otherwise conventional manner (usually at elevated temperatures in the range from 270° F. (132° C.) to 380° F. (193° C.)), thus resulting in uniform distribution of the paramagnetic ions throughout the tube.

Alternatively, it is possible to provide the paramagnetic ions only in a portion of the tube, such as a distal portion, or in a plurality of circumferential bands axially spaced apart along the tube. Provision of such lengths and/or bands of paramagnetic ions can be achieved by periodically introducing the paramagnetic ionic particles into the polymeric material. As a further alternative, the paramagnetic ions can be provided along an axial line or stripe of the flexible tubing, e.g. by introducing the paramagnetic ionic particles into the extruder at one circumferential region of the tube as it is extruded.

In contrast to prior methods (such as disclosed in U.S. Pat. No. 5,154,179 and Rubin et al. (1990), supra.), the present invention in one aspect relies on the incorporation of very small iron ($Fe_2O_3$, $Fe_3O_4$, and elemental iron) particles of 20 μm or smaller size, such as superparamagnetic iron oxide particles, which allow for a large number (high concentration) to be present near an internal surface or external surface of the catheter or other devices. When a sufficiently large number of particles is present in these locations, they are capable of significantly shortening the relaxation times of adjacent water protons. The effect of such high surface concentrations of iron particles causes an increased signal intensity of the water contained within the lumen of the catheter or other device and adjacent to its outer surface, and this increased signal intensity is seen in all orientations of the catheter, whether perpendicular to or parallel with the external magnetic field. In contrast, the catheters of U.S. Pat. No. 5,154,179 and Rubin et al. (1990) exhibit no image enhancement when oriented parallel to the MR field. Thus, it is believed that the particle sizes employed were sufficiently large to decrease surface concentrations of the ferromagnetic iron oxide particles.

Catheters prepared with iron oxide particles of less than 1 μm size according to the present invention produce increased signal intensity of the water within the lumen of the catheters. This phenomenon is found to be inversely proportional to the concentration of the iron oxide particles when the catheters were parallel with the static magnetic field, but the highest signal intensity occurred at 0.5% weight volume when the catheters were perpendicular to the external magnetic field. This phenomenon is apparently related to an increased susceptibility effect seen when the catheters are perpendicular to the external field (see Table 2 in the Experimental section hereinafter).

The important determining factor appears to be the number of particles distributed on the surface of the catheter. A homogenous distribution of relatively small particles throughout the catheter wall will mitigate susceptibility effects within the catheter wall itself (the artifacts described in U.S. Pat. No. 5,154,179 and Rubin et al. (1990), supra.). Another important difference is that the useful signal for identifying a catheter is produced by the influence of the small iron oxide particles on the water protons adjacent to the surface of the catheter. This useful signal is not present with large ferromagnetic iron particles, as described in Rubin et al.

Although the size distribution of iron particles clearly encompasses superparamagnetic, single domain particles (e.g., <50 nm), this effect also occurs with iron particles which are less than 1 $\mu$m in size. With proper formulation, this effect should occur with particles up to 20 $\mu$m in size. As used herein, particle size refers to average particle size measured by conventional techniques, e.g., laserlight scattering for particles sized on the order of microns and X-ray diffraction for smaller particles sized on the order of nanometers. Such measurement techniques are well known in the art. Conveniently, iron and iron oxide particles in the desired size ranges can be obtained commercially from vendors such as Aldrich Chemical Co., Milwaukee, Wis. 53201.

Large iron particles increase the magnetic moment of each center and thus increase the susceptibility artifact. However, for comparable weights, large particle size will decrease the number of particles present along the outer or inner surface of the catheter, and, thereby, decrease the influence of the particles on the water protons present near the surface of the catheter. Smaller iron oxide particles in the superparamagnetic range and up to about 20 $\mu$m will reduce the susceptibility differences within the wall of the catheter and provide more particles along the catheter surface, thereby increasing the potential to shorten relaxation times within water molecules adjacent to the catheter's surface to provide an image enhancement in all orientations relative to the main magnetic field.

Preferred superparamagnetic particles according to the present invention may be any single domain sized particles displaying superparamagnetic properties, typically being an iron oxide. Exemplary compounds include $Fe_2O_3$, $Fe_3O_4$, and elemental iron, each with a crystal size below about 5 nm, preferably being in the range from about 1 nm to 3 nm. Specific methods for preparing the preferred superparamagnetic particles are described in Chambron et al. (1993) Magnetic Resonance Imaging 11:509–519, the full disclosure of which is incorporated herein by reference.

The superparamagnetic and/or other small iron particles will be fixedly incorporated within the body of or over the surface of the non-metallic member of the article of the present invention during fabrication. By "fixedly incorporated," it is meant that the particles are dispersed or otherwise incorporated directly within or coated over the material matrix of the non-metallic member. This may be accomplished by various conventional techniques, such as extrusion, impregnation, compounding, lamination, coating, painting, chemical vapor deposition (CVD), or the like. In the case of organic polymers, fixed incorporation within the material matrix will preferably be accomplished by combining the small iron and/or superparamagnetic particles with a suitable polymeric material prior to forming it to the desired article, typically by extrusion, injection molding, or the like. Alternatively, the particles may be coated or layered over the article by conventional coating techniques, such as applying a suspension of the particles in a liquid phase which can be dried or cured (e.g., cross-linked) to cover the exterior of the article.

The superparamagnetic and/or other small iron particles will be incorporated in the non-metallic member in an amount or concentration sufficient to achieve the desired image enhancement. The particular amount or concentration depends on the strength of the magnetic particles, the nature of the non-metallic material, and a variety of other factors, but will usually be in the range from 0.001% to 1% by weight, more usually being in the range from 0.01% to 0.5% by weight, and frequently being in the range from 0.1% to 0.5% by weight when the particles are uniformly dispersed. Lower overall concentrations may be used when the particles are applied or concentrated at or near the exterior surface of the article.

The iron particles need not be dispersed throughout the entire volume of the non-metallic member since they act only at or near the surface. In particular, the superparamagnetic and small iron particles act by shortening the relaxation time of the hydrogen atoms in surrounding aqueous and body fluids, e.g., body fluids such as blood, effusions, and the like. The effect, however, acts over a limited distance, so only those particles which are present to a depth of about 5 $\mu$m from the exterior and/or interior surface, preferably about 50 nm, will be effective. Thus, in particular embodiments, the superparamagnetic and other small iron particles are preferably localized or concentrated within such exterior regions of the non-metallic member.

Exemplary flexible tubes may be prepared according to the method of the present invention using conventional extrusion equipment and techniques. Such extruders utilize polymeric materials and, by applying heat and pressure, form the polymer to a continuous length of tubing having a desired diameter, a wall thickness, and the like. The small iron and/or superparamagnetic particles of the present invention may be incorporated into such tubes simply by mixing the particles with the polymeric starting material prior to extrusion. Uniform dispersion of the particles can thus be achieved by completely mixing and dispersing the particles within the polymeric material at the desired weight and concentration and extruding the mixture in an otherwise conventional manner, thus resulting in uniform distribution of the small iron and/or superparamagnetic particles throughout the tube.

Alternatively, it is possible to provide the small iron and/or superparamagnetic materials only in a portion of the tube, such as a distal portion, or in a plurality of circumferential bands axially spaced apart along the tube, or in an annular film or layer disposed over a portion or all of the exterior surface of the device. Provision of such lengths and/or bands of particles can be achieved by periodically introducing the small iron and/or superparamagnetic particles into the polymer. As a further alternative, the small iron and/or superparamagnetic particles can be introduced along an axial line or stripe of the flexible tubing, e.g., by introducing the particles into the extruder at one circumferential region of the tube as it is extruded. Annular layers can be introduced at the time of extruding or after extrusion by coating the finished tube.

Referring now to FIG. 1, an exemplary catheter device constructed in accordance with the principles of the present invention is illustrated. The catheter 10 comprises an elongate body in the form of a flexible polymeric tube 12. The tube may be formed by any of the techniques described above, and includes an outwardly flared conical proximal end 14 and a generally sealed, blunt end 16. A plurality of aspiration/perfusion ports 18 are formed near the distal end of the catheter, and an axial lumen 20 permits fluid to be introduced or aspirated through the ports 18 via the proximal end 14. The catheter 10 is thus useful as a drainage catheter, perfusion catheter, or the like. In one embodiment of FIG. 1, paramagnetic ionic particles are fixedly incorporated and dispersed uniformly in the polymer material of catheter 10. Alternatively, in another embodiment of FIG. 1, small iron and/or superparamagnetic particles are fixedly incorporated and dispersed in the polymer material at least at or near an exposed surface of catheter 10, for example the outer surface 13 of the catheter and/or the inner surface 19 surrounding lumen 20.

Figure 2:
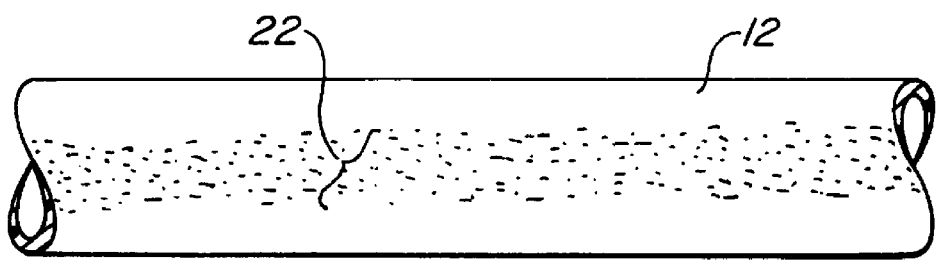
FIG. 2 illustrates a section of the catheter of FIG. 1, with the paramagnetic ions or the iron particles being concentrated in an axial stripe, rather than being uniformly dispersed therethrough.

As illustrated in FIG. 2, the catheter 10 of FIG. 1 may be fabricated to include only a single stripe 22 of paramagnetic ionic particles or small iron and/or superparamagnetic particles running axially along its length. The stripe 22 can be formed by introducing the particles selectively about the circumference of the extruder, as described above.

It will be appreciated that the methods and the medical devices, such as flexible tubes, of the present invention can be utilized to form a variety of other types, such as angioplasty catheters, atherectomy catheters, introducer sheaths, intracardiac catheters, and the like.

gadolinium loading, typically about 1.5% gadolinium and 10–15% water.

Preparation of Catheters

Preparation of the catheter was accomplished by hand mixing the LZ-Y54 paramagnetic ionic particles prepared above (1% weight/weight) into low density polyethylene. The mixture was extruded at 280° F. (138° C.) using a Harrel Extruder (Norwalk, Conn.) to form a tubular member.

Magnetic Resonance Imaging of the Material

Two catheters prepared as described above were completely submerged in water in test tubes and placed vertically in a test tube rack which was placed inside a 1.5 Tesla MRI scanner (GE Medical Systems, Milwaukee, Wis.). A control tube (without paramagnetic ionic particles), and air and water standards were also placed in the rack. Signal intensities and standard deviations were measured in regions of interest (ROI's), and the results are shown in Table 1. Three pulsing sequences which were used to evaluate the catheter materials were as follows:

(1) T1 sequence: TR/TE, 300/15/fr (fraction/echo), 16 KHz, 22 cm field of view, 10 mm slice thickness with no inter slice skip. 256×256 matrix, 1 NEX.

(2) T2 (spin echo) sequence: TR/TE, 2500/20/80, 16 KHz, 22 cm field of view, 10 mm slice thickness, 256×256 matrix, 1 NEX.

(3) GRASS (Gradient echo) sequence: TR/TE 133/5/ fractional echo, 60° tip angle, 16 KHz, 22 cm field of view, 10 mm slice thickness, no gap, 256×256 matrix, 2 NEX.

TABLE 1

| Pulsing Sequence | Signal Intensities | | | | |
| --- | --- | --- | --- | --- | --- |
| | Catheters | | | Water | Air |
| | Control | #1 | #2 | | |
| T1 | 145.0 ± 48.9 | 158.0 ± 39.0 | 154.9 ± 31.8 | 524.8 ± 19.7 | 8.7 ± 5.2 |
| T2 (1st) | 810.0 ± 239.1 | 841.1 ± 151.2 | 897.3 ± 137.2 | 1751.1 ± 11.9 | 9.8 ± 4.9 |
| T2 (2nd) | 650.2 ± 205.9 | 705.1 ± 141.2 | 730.0 ± 113.5 | 1495.9 ± 12.4 | 10.4 ± 6.0 |
| GRASS | 208.1 ± 136.4 | 249.9 ± 109.0 | 264.0 ± 80.3 | 670.6 ± 13.3 | 6.3 ± 4.1 |

The following examples are offered by way of illustration, not by way of limitation.

EXAMPLE 1

Preparation of Paramagnetic Ionic Particles

Sodium chloride (29.2 g) was dissolved in one liter distilled water. Fifty grams of LZ-Y54 zeolite (UOP, Des Plaines, Ill.) was then added to the solution and stirred for 12 to 24 hours. The hydrated zeolite was collected by suction filtration and washed with distilled water until the filtrate tested negative for chloride ion. The hydrated zeolite was transferred to one liter of distilled water and the pH was adjusted to 4.8 by addition of 0.1N HCl. $GdCl_3.6H_2O$ (16.0 g) was dissolved in 500 mL of distilled water and added to the zeolite suspension which was then stirred for 3 to 6 hours. The solid was collected by suction filtration and washed with distilled water. The resulting paramagnetic ionic particles were then air dried. Samples were taken and assayed for water content and gadolinium content. Typically, the LZ-Y54 zeolite contained about 8.5% gadolinium and 20–25% water. Other zeolites such as CBV-720 (PQ Corporation, Valley Forge, Pa.) can be prepared following similar procedures, but have been found to provide a lower A 9% increase in signal intensity over control was measured on the T1 sequence. A 12% increase in signal intensity over control was measured on the second echo of the spin echo sequence. A 27% increase in signal intensity over control was measured on the GRASS sequence. These data indicate that the signal intensity is increased by the inclusion of paramagnetic ionic particles in the polyethylene structure of the catheter wall.

EXAMPLE 2

Iron oxide ($Fe_2O_3$) particles having an average particle size below 1 $\mu$m were obtained from Aldrich Chemical Co., Milwaukee, Wis. 53201, and extruded uniformly into polyethylene tubing having a diameter of 1 mm at concentrations of 1%, 0.5%, and 0.1% by weight, following the procedures of Example 1. Tubing having the same diameter and composition but without the iron oxide was also extruded. Bundles of the tubing with and without the iron oxide were scanned at 1.5 T (submerged in water) following the procedures of Example 1.

The results are set forth in Table 2 below. Signal intensities were highest for the 0.1% iron oxide tubing, being 47% higher than the control tubing. The other two concentrations were respectively lower due to the increase T2 effects of the iron oxide particles at higher concentration in the wall (tubing parallel to $B_o$ only). High signal intensities were seen in both parallel and perpendicular orientations relative to the $B_o$ (static magnetic field). The signal intensities were slightly lower when the tubes were perpendicular to the magnetic field. This may be due to an increased susceptibility phenomenon as described in Rubin et al. (1990), supra.

TABLE 2

| Relative to $B_o$ Orientation | Signal Intensity | | | |
| --- | --- | --- | --- | --- |
| | 0.1% | 0.5% | 1.0% | Control |
| Parallel | 77.6 ± 20.8 | 69.7 ± 23 | 59.4 ± 23.1 | 52.7 ± 13.4 |
| Perpendicular | 68.7 ± 23.0 | 57.0 ± 16.5 | 56.7 ± 23.0 | 58.2 ± 16.6 |

T1 = 300/15 (Tr/TE), 1.5 Tesla

EXAMPLE 3

Figure 3:
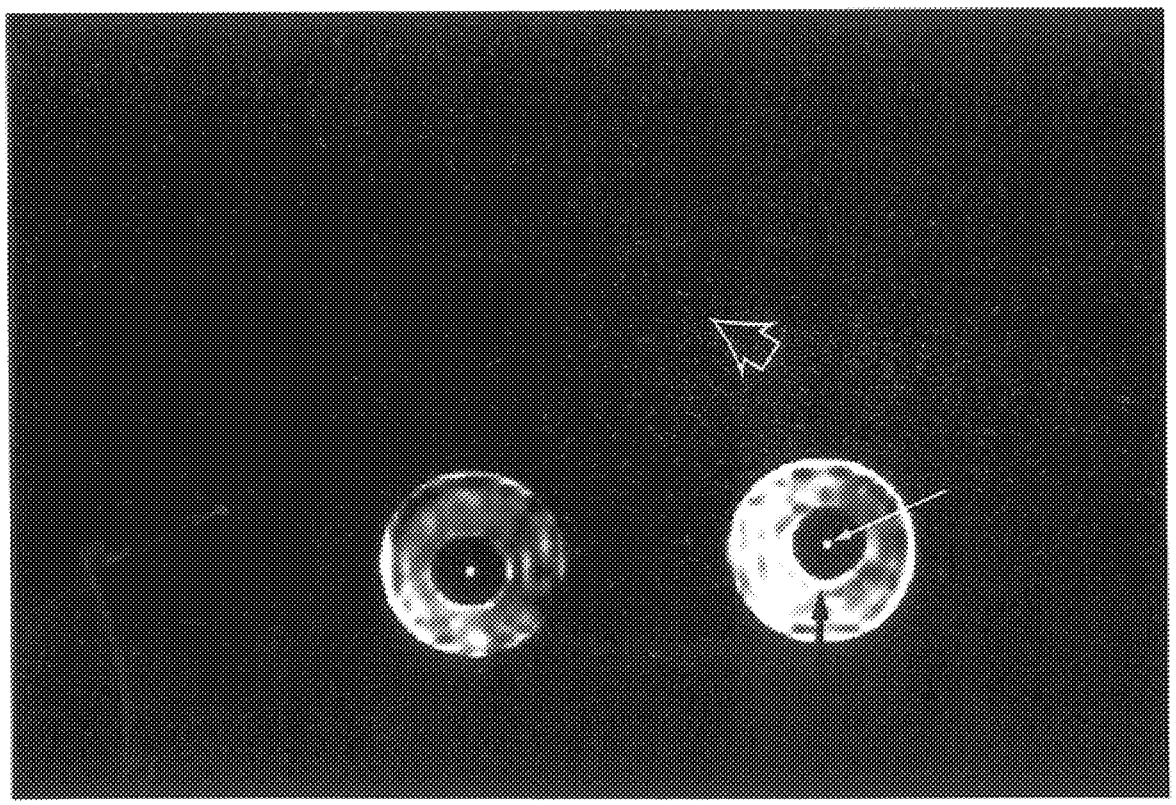
FIG. 3 is a photoradiograph of a control tubing (above with open, white arrow), 3-inch tubing with iron oxide (left, no arrow), and 4-inch tubing with iron oxide (right, solid arrow) under magnetic resonance imaging.

Following the procedures of Example 2, polyethylene tubing was extruded, the tubing having a diameter of 3 in. (7.6 cm) and containing iron oxide particles (average particle size of 80 nm) uniformly dispersed therein at a concentration of 0.5% w/w. Identical tubing but with a diameter of 4 in. (10.2 cm) was also extruded. Tubing having the same composition but without the iron oxide particles was likewise prepared as a control. Specimens of each of the tubing were suspended in water inside test tubes, and an axial MRI scan was obtained. The specimens were oriented with the long axis parallel to the static magnetic field (B-0). A photoradiograph of the three specimens is shown in FIG. 3. MR images of the control tubing (positioned above in the picture, indicated by open white arrow), 3 in. tubing with iron oxide (left, no arrow) and 4 in. tubing with iron oxide (right, solid arrows) are shown. Water in the center of the catheters with iron oxide contrast agent in the wall has an increased signal intensity (white dot indicated by long white arrow, 4 in. tubing), and a similar increase in water signal intensity is seen surrounding the tubing (black arrow). The actual tubing wall is seen as a black structure traversed by the head of the long white arrow. Similar findings are seen in the 3 in. tubing containing iron oxide. Water surrounding the control tubing (with no iron oxide contrast agent in the wall) has a much lower signal intensity than water surrounding the surface of the tubing with contrast media contained within their walls.

The MRI images were obtained at 1.5 Tesla using a T1 weighted pulsing sequence (TR/TE, 300/15, 256×256, 2 nex, 16 kHz band width).

Although the foregoing invention has been described in some detail by way of illustration and example, for purposes of clarity of understanding, it will be obvious that certain changes and modifications may be practiced within the scope of the appended claims.

What is claimed is:

1. An article for use in internal medical procedures, said article comprising a flexible non-metallic member composed of an organic polymer having paramagnetic ionic particles dispersed directly in a material matrix thereof at a concentration effective to enhance detectability of at least a portion of the article when viewed by magnetic imaging when the article is present in an aqueous environment, which enhancement is irrespective of the orientation of the article in the magnetic field, wherein the concentration of paramagnetic ionic particles in the material matrix is in the range from 0.1% to 20% by weight.

2. An article as in claim 1, wherein the elongate flexible member is a tubular catheter.

3. An article as in claim 1, wherein the article is a catheter having an enhanced magnetic image, wherein, the non-metallic member is a tubular member having a proximal end, a distal end, and at least one lumen extending therethrough and being composed of an organic polymer; and the paramagnetic ionic particles are fixedly incorporated in selected portions of the tubular member at a concentration effective to enhance detectability of said selected portion when viewed by magnetic imaging.

4. An article as in claim 1, 2, or 3, wherein the paramagnetic ionic particles are incorporated uniformly throughout the non-metallic member.

5. An article as in claim 1, 2, or 3, wherein the paramagnetic ionic particles are incorporated non-uniformly within the non-metallic member.

6. An article as in claim 3, wherein the paramagnetic ionic particles are incorporated substantially uniformly throughout the tubular member, whereby the entire catheter will have an enhanced magnetic resonance image.

7. An article as in claim 3, wherein the paramagnetic ionic particles are incorporated in a preselected pattern in the tubular member, whereby only portions of the catheter will have an enhanced magnetic resonance image.

8. An article as in claim 7, wherein the preselected pattern includes one or more axial bands formed in the tubular member.

9. An article as in claim 1 or 3, wherein the paramagnetic ionic particles comprise paramagnetic metal ions entrapped in a carrier particle with a proton-donating fluid.

10. An article as in claim 9, wherein the entrapped ions are selected from the group consisting of elements having atomic numbers 21–29, 42, 44, and 58–70.

11. An article as in claim 9, wherein the proton-donating fluid is water, an alcohol, a glycerol, a sulfonated detergent, an ether, an amine, or a imidazole.

12. An article as in claim 9, wherein the carrier particle is a natural or synthetic zeolite, a molecular sieve, a clay, or a synthetic ion exchange resin.

13. An article as in claim 9, wherein the entrapped ions are $Gd^{+3}$, the proton-donating fluid is water, and the ion exchange resin is a type Y zeolite.

14. An article as in claim 1 or 3, wherein the non-metallic member is substantially free from ferromagnetic materials.

15. An article as in claim 1 or 3, wherein the non-metallic member further includes radiopaque material.

16. A method for imaging a catheter within a patient's body, said method comprising:

introducing to the patient's body a catheter comprising a non-metallic member having paramagnetic ionic particles dispersed directly in a material matrix thereof at a concentration in the material matrix in the range from 0.1% to 20% by weight; and imaging the body using a magnetic imaging device, whereby the catheter will produce an image which will have enhanced detectability irrespective of the orientation of the catheter to the magnetic field.

17. A method as in claim 16, wherein the non-metallic member is composed of an organic polymer and the paramagnetic ionic particles comprise paramagnetic metal ions entrapped together with a proton-donating fluid in a carrier particle.

18. A method as in claim 17, wherein the proton-donating fluid is water.

19. A method as in claim 17, wherein the carrier particle is an ion exchange resin.

20. A method as in claim 18, wherein the carrier particle is an ion exchange resin.

21. An article for use in internal medical procedures, said article comprising a non-metallic member having paramagnetic ions entrapped in carrier particles with a proton-donating fluid fixedly incorporated therein at a concentration effective to enhance detectability of at least a portion of the article when viewed by magnetic imaging when the article is present in an aqueous environment, which enhancement is irrespective of the orientation of the article in the magnetic field.

22. An article as in claim 21, wherein the non-metallic member is an elongate flexible member.

23. An article as in claim 22, wherein the elongate flexible member is composed of an organic polymer.

24. An article as in claim 23, wherein the elongate flexible member is a tubular catheter.

25. An article as in claim 21, wherein the article is a catheter having an enhanced magnetic image, wherein, the non-metallic member is a tubular member having a proximal end, a distal end, and at least one lumen extending therethrough and being composed of an organic polymer; and the particles are fixedly incorporated in selected portions of the tubular member at a concentration effective to enhance detectability of said selected portion when viewed by magnetic imaging.

26. An article as in claim 21, 22, 23, 24, or 25, wherein the particles are incorporated uniformly throughout the non-metallic member.

27. An article as in claim 21, 22, 23, 24, or 25, wherein the particles are incorporated non-uniformly within the non-metallic member.

28. An article as in claim 25, wherein the particles are incorporated substantially uniformly throughout the tubular member, whereby the entire catheter will have an enhanced magnetic resonance image.

29. An article as in claim 25, wherein the particles are incorporated in a preselected pattern in the tubular member, whereby only portions of the catheter will have an enhanced magnetic resonance image.

30. An article as in claim 29, wherein the preselected pattern includes one or more axial bands formed in the tubular member.

31. An article as in claim 21, wherein the entrapped ions are selected form the group consisting of elements having atomic numbers 21–29, 42, 44, and 58–70.

32. An article as in claim 21, wherein the proton-donating fluid is water, an alcohol, a glycerol, a sulfonated detergent, an ether, an amine, or a imidazole.

33. An article as in claim 21, wherein the carrier particle is a natural or synthetic zeolite, a molecular sieve, a clay, or a synthetic ion exchange resin.

34. An article as in claim 21, wherein the entrapped ions are $Gd^{+3}$, the proton-donating fluid is water, and the ion exchange resin is a type Y zeolite.

35. An article as in claim 21 or 25, wherein the non-metallic member is substantially free from ferromagnetic materials.

36. An article as in claim 21 or 25, wherein the non-metallic member further includes radiopaque material.

37. An article as in claim 21 or 25, wherein the concentration of paramagnetic ionic particles is in the range from 0.1% to 20% by weight.

38. A method for imaging an article within a patient's body, said method comprising:

introducing to the patient's body an article comprising a non-metallic member having paramagnetic ionic particles fixedly incorporated therein wherein the non-metallic member is composed of an organic polymer and the paramagnetic ionic particles comprise paramagnetic metal ions entrapped together with a proton-donating fluid in a carrier particle; and imaging the body using a magnetic imaging device, whereby the article will produce an image which will have enhanced detectability irrespective of the orientation of the article to the magnetic field.

39. A method as in claim 38, wherein the article comprises a catheter.

40. A method as in claim 39, wherein the article comprises an implant.

41. A method as in claim 38, wherein the proton-donating fluid is water.

42. A method as in claim 38, wherein the carrier particle is an ion exchange resin.

43. A method as in claim 38, wherein the carrier particle is an ion exchange resin.

44. An article for use in internal medical procedures, said article comprising a tubular member composed of an organic polymer having paramagnetic ions extruded therein at a concentration effective to enhance detectability of at least a portion of the article when viewed by magnetic imaging when the article is present in an aqueous environment, which enhancement is irrespective of the orientation of the article in the magnetic field, wherein the paramagnetic ions are entrapped in a carrier particle with a proton-donating fluid elected from the group consisting of water, an alcohol, a glycerol, a sulfonated detergent, an ether, an amine, or a imidazole.

45. An article as in claim 44, wherein the paramagnetic ions are incorporated substantially uniformly throughout the tubular member, whereby the entire catheter will have an enhanced magnetic resonance image.

46. An article as in claim 44, wherein the paramagnetic ions are incorporated in a preselected pattern in the tubular member, whereby only portions of the catheter will have an enhanced magnetic resonance image.

47. An article as in claim 46, wherein the preselected pattern includes one or more axial bands formed in the tubular member.

48. An article as in claim 44, wherein the extruded paramagnetic ions are selected form the group consisting of elements having atomic numbers 21–29, 42, 44, and 58–70.

49. An article as in claim 44, wherein the carrier particle is a natural or synthetic zeolite, a molecular sieve, a clay, or a synthetic ion exchange resin.

50. An article as in claim 49, wherein the entrapped ions are $Gd^{+3}$, the proton-donating fluid is water, and the ion exchange resin is a type Y zeolite.

51. An article as in claim 49, wherein the tubular member is substantially free from ferromagnetic materials.

52. An article as in claim 44, wherein the tubular member further includes radiopaque material.

53. An article as in claim 44, wherein the concentration of paramagnetic ions is in the range from 0.1% to 20% by weight.

54. A method for imaging an article within a patient's body, said method comprising:

introducing to the patient's body an article comprising a tubular body composed of an organic polymer having paramagnetic ions extruded therein; and imaging the body using a magnetic imaging device, whereby the article will produce an image which will have enhanced detectability irrespective of the orientation of the article to the magnetic field, wherein the paramagnetic ions are entrapped in a carrier particle with a proton-donating fluid elected from the group consisting of water, an alcohol, a glycerol, a sulfonated detergent, an ether, an amine, or a imidazole.

55. A method as in claim 54, wherein the article comprises a catheter.

56. A method as in claim 54, wherein the carrier particle is a natural or synthetic zeolite, a molecular sieve, a clay, or a synthetic ion exchange resin.

57. A method as in claim 56, wherein the entrapped ions are $Gd^{+3}$, the proton-donating fluid is water, and the ion exchange resin is a type Y zeolite.

58. A method as in claim 56, wherein the tubular member is substantially free from ferromagnetic materials.

59. A method for imaging an implant within a patient's body, said method comprising:

introducing to the patient's body an implant comprising a non-metallic member having paramagnetic ionic particles dispersed directly in a material matrix thereof at a concentration in the material matrix in the range from 0.1% to 20% by weight; and imaging the body using a magnetic imaging device, whereby the implant will produce an image which will have enhanced detectability irrespective of the orientation of the implant to the magnetic field.

60. A method as in claim 59, wherein the non-metallic member is composed of an organic polymer and the paramagnetic ionic particles comprise paramagnetic metal ions entrapped together with a proton-donating fluid in a carrier particle.

61. A method as in claim 60, wherein the proton-donating fluid is water.

62. A method as in claim 60 wherein the carrier particle is an ion exchange resin.

63. A method as in claim 60, wherein the carrier particle is an ion exchange resin.

64. A method for imaging an article within a patient's body, said method comprising:

introducing to the patient's body an article comprising a non-metallic member having paramagnetic ionic particles dispersed directly in a material matrix thereof at a concentration in the material matrix in the range from 0.1% to 20% by weight, wherein the non-metallic member is composed of an organic polymer and the paramagnetic ionic particles comprise paramagnetic metal ions entrapped together with a proton-donating fluid in a carrier particle; and imaging the body using a magnetic imaging device, whereby the article will produce an image which will have enhanced detectability irrespective of the orientation of the article to the magnetic field.

65. A method as in claim 64, wherein the article comprises a catheter.

66. A method as in claim 64, wherein the article comprises an implant.

67. A method as in claim 64, wherein the proton-donating fluid is water.

68. A method as in claim 64, wherein the carrier particle is an ion exchange resin.

69. A method as in claim 67, wherein the carrier particle is an ion exchange resin.

* * * * *